United States Patent
Razavi et al.

[11] Patent Number: 6,002,033
[45] Date of Patent: Dec. 14, 1999

[54] BRIDGED METALLOCENES FOR USE IN CATALYST SYSTEMS

[75] Inventors: Abbas Razavi, Mons; Dominique Vereecke, Dilbeek, both of Belgium

[73] Assignee: Fina Research, S.A., Feluy, Belgium

[21] Appl. No.: 09/096,883

[22] Filed: Jun. 12, 1998

Related U.S. Application Data

[62] Division of application No. 08/562,319, Nov. 22, 1995, abandoned.

[51] Int. Cl.$^6$ .............................. C07F 17/00; C07F 7/00
[52] U.S. Cl. .............................. 556/11; 556/53; 526/126; 526/160; 526/943; 502/103; 502/117
[58] Field of Search ................. 556/11, 53; 502/103, 502/117; 526/126, 160, 943

[56] References Cited

U.S. PATENT DOCUMENTS

| | | | |
|---|---|---|---|
| 5,145,819 | 9/1992 | Winter et al. | 502/117 |
| 5,243,001 | 9/1993 | Winter et al. | 526/127 |
| 5,486,585 | 1/1996 | Murata et al. | 526/130 |

FOREIGN PATENT DOCUMENTS

| | | |
|---|---|---|
| 0420436 | 4/1991 | European Pat. Off. . |
| 0351392 | 1/1994 | European Pat. Off. . |
| 0577581 | 1/1994 | European Pat. Off. . |
| 0582195 | 2/1994 | European Pat. Off. . |
| 0608054 | 7/1994 | European Pat. Off. . |

OTHER PUBLICATIONS

"Stereospecific Olefin Polymerization with Chiral Metallocene Catalysts", H.H. Brintzinger et al, Angew, Chem. Int. Ed. Engl., vol. 34, pp. 1143–1170 (1995).

*Primary Examiner*—Porfirio Nazario-Gonzalez
*Attorney, Agent, or Firm*—Jimmy D. Wheelington; M. Norwood Cheairs

[57] ABSTRACT

Bridged metallocenes of Group IVb metals provide improved results when the bridge comprises a neutral electron-donor substituent of general formula $$R''' \, Z \, R''''_j$$

wherein
R''' is a rigid unsaturated hydrocarbon radical between Z and the bridge, such that Z is separated from the bridge by 2 to 5 carbon atoms
Z is nitrogen, phosphorus, oxygen or sulphur,
R'''' is H or an alkyl, cycloalkyl, aryl, alkylaryl or arylalkyl having a maximum of 15 carbon atoms, each R'''' being the same or different,
j is 1 when Z=O or S and 2 when Z=N or P.

21 Claims, 2 Drawing Sheets

BRIDGED METALLOCENES FOR USE IN CATALYST SYSTEMS

This application is a division of application Ser. No. 08/562,319 filed Nov. 22, 1995 now abandoned.

BACKGROUND OF THE INVENTION

1. Field of the Invention

This invention relates to bridged metallocene compounds. More particularly, it relates to bridged dicyclopentadienide derivatives of Group IVb metals. It also relates to the use thereof in catalyst systems for the polymerization of olefins.

2. Description of the Prior Art

Metallocene catalysts suffer from a disadvantage in that the polyolefin product has small particle size and low bulk density. There is therefore a need in the art for a catalyst system that would retain advantages for metallocene catalyst systems but eliminate the above-mentioned disadvantage thereof.

Morphology improvements have generally been obtained by immobilizing the metallocene on an inorganic carrier or on an organic functionally active carrier, for the purpose of heterogenization.

U.S. Pat. No. 5,145,819 and 5,243,001 and EP-A-582195 disclose bridged metallocenes wherein alkoxy substituents can be attached directly to the bridge.

EP-A-608054 generically discloses bridged metallocenes wherein the bridge may have as substituent a 1–20 C hydrocarbyl containing oxygen, phosphorus, nitrogen or sulphur.

SUMMARY OF THE INVENTION

Accordingly, an object of this invention is to provide bridged metallocenes for use in catalyst systems which produce polyolefins with little or no small particle size.

Another object of this invention is to provide bridged metallocenes for use in catalyst systems which produce polyolefins with high bulk density.

A further object is to provide bridged metallocenes which when used do not give reactor fouling or crust formation.

These and other objects are accomplished by the use of a neutral electron-donor substituent on the bridge of bridged metallocenes as described and claimed below.

BRIEF DESCRIPTION OF THE DRAWINGS

A more complete appreciation of the invention and many of the attendant advantages thereof will be readily understood by reference to the following detailed description when considered in connection with the accompanying drawings in which like numerals in different figures represent the same structures or elements wherein.

DETAILED DESCRIPTION OF THE INVENTION

Figure 1:
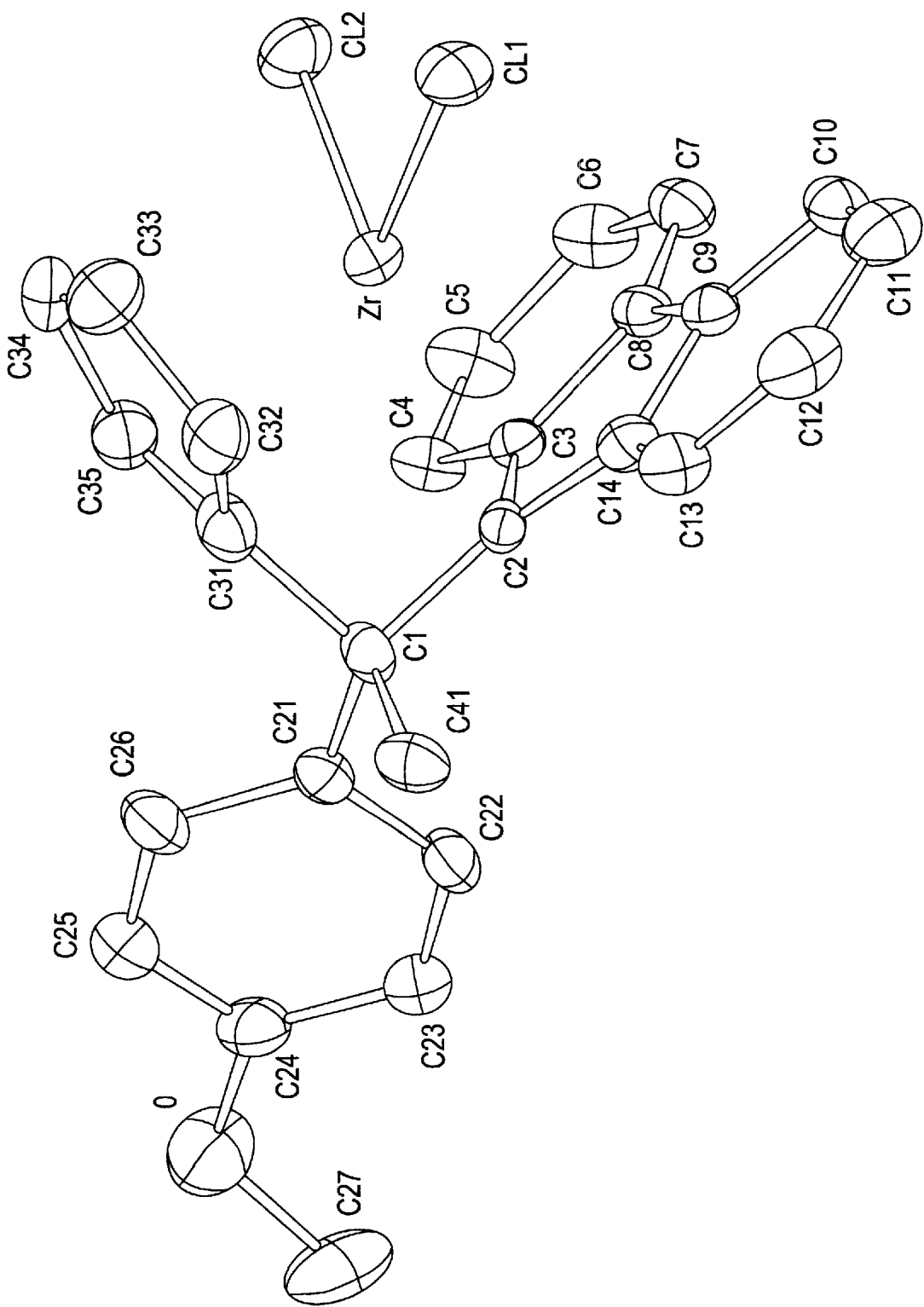
FIGS. 1 and 2 are representations of the structure of $(Cp)(Flu)C(CH_3)(p\text{-}PhOCH_3)ZrCl_2$.

The present invention provides for the use of a neutral electron-donor substituent on the bridge of bridged metallocenes, said substituent having the formula

wherein

R''' is a rigid unsaturated hydrocarbon radical between Z and the bridge, such that Z is separated from the bridge by 2 to 5 carbon atoms, Z is nitrogen, phosphorus, oxygen or sulphur, R'''' is H or an alkyl, cycloalkyl, aryl, alkylaryl or arylalkyl having a maximum of 15 carbon atoms, each R'''' being the same or different, j is 1 when Z=O or S and 2 when Z=N or P.

More specifically, the preferred bridged metallocenes (i.e. bridged dicyclopentadienide derivatives) of Group IVb metals are of the general formula

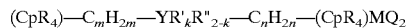

wherein

M is a Group IVb metal (Ti, Zr, Hf),

Q is a hydrocarbyl radical having from 1 to 20 carbon atoms or a halogen, each Q being the same or different, Cp is a cyclopentadienyl ring, R is a substituent on a cyclopentadienyl ring and can be H or a hydrocarbon radical having 1 to 9 carbon atoms, each R being the same or different, each $(CpR_4)$ being the same or different, m is 0, 1, 2 or 3, n is 0, 1, 2, or 3, m+n is 0, 1, 2 or 3, k is 1 or 2

Y is C or Si

R' is a neutral electron-donor substituent of general formula

R'''Z R''''$_j$ wherein

R''' is a rigid unsaturated hydrocarbon radical between Z and the bridge, such that Z is separated from the bridge by 2 to 5 carbon atoms Z is nitrogen, phosphorus, oxygen or sulphur, R'''' is H or an alkyl, cycloalkyl, aryl, alkylaryl or arylalkyl having a maximum of 15 carbon atoms, each R'''' being the same or different, j is 1 when Z=O or S and 2 when Z=N or P, R'' is as indicated for R''''.

The preferred Group IVb metals are hafnium and zirconium, the most preferred being zirconium. The preferred Q is a hydrocarbyl radical having 1 to 3 carbon atoms or a halogen, the most preferred being chlorine or bromine. As to the $CpR_4$ components, they are selected according to the principles known in the art, in order to obtain the desired properties of the polymer.

Whilst not wishing to be bound by a theory, it is believed that this invention lies in the improvement provided by the R' substituent(s) on the bridge as compared to the same bridged metallocene without R' substituent(s).

As to the bridge, m and n are preferably 0, and Y is preferably C.

As to the R' bridge substituent(s), k is preferably 1, R''' preferably forms aromatic ring and is most preferably p-phenylidene, Z is preferably O or N, and R'''' is preferably H or methyl or ethyl (most preferably methyl or ethyl).

As to the R''0 bridge substituent, it is preferably H or alkyl up to 4 carbon atoms or aryl, most preferably H or methyl.

The metallocene can be prepared by any suitable method e.g. as described in U.S. Pat. No. 5,117,020, hereby incorporated by reference. A particularly suitable method for preparing fulvenes is described in the Examples, based on the methods by Stone and Little, J. Org. Chem., vol.49, p. 1849 (1984), and Kresze and Goetz Chem. Ber., vol. 90, p. 2161, (1957), both hereby incorporated by reference.

The present invention further provides a catalyst system essentially consisting of one or more of the bridged metallocenes of the invention together with one or more co-catalysts. The preferred co-catalysts are those of the alumoxane type, preferably methylalumoxane, which are well known in the art and need not be described here. The bridged metallocenes can be supported, but are preferably unsupported for the purpose of this invention; suitable supports and techniques for supporting metallocenes are also well known in the art and need not be described here; the preferred co-catalysts for supported bridged metallocenes are of the alkylaluminum type, preferably trialkylaluminum, which are well known in the art and need not be described here.

The polymerization and, where applicable, prepolymerization conditions are well known in the art and need not be described here. The catalyst systems of the invention can be used to polymerize olefins, particularly ethylene, propylene or a mixture thereof, most particularly propylene.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1 Catalyst Based on (Cp)(Flu)C(CH$_3$) (p-PhOCH$_3$)ZrCl$_2$ a. Preparation of the fulvene To a solution of freshly distilled cyclopentadiene (0.625 mol) and p-methoxyacetophenone (0.25 mol) in reagent grade methanol (360 ml) was added pyrrolidine (0.375 mol, freshly distilled under N$_2$).

The mixture was stirred under nitrogen at room temperature for 20 hours.

Acetic acid (23 ml) was then added to the solution. The reaction mixture was diluted with ether and water (100 ml each). The aqueous portion was washed with ether (2×250 ml) and the combined organics were washed with water and brine (50 ml each), then dried over MgSO$_4$ and concentrated in vacuo.

Purification by recrystallization from methanol affords 30 g of 6-(4-methoxy-phenyl) 6-methyl-fulvene.

Yield: 61%. Melting point (M.P.): 66–67° C.

b. Preparation of the ligand.

41.5 grams (0.25 mol) of fluorene were dissolved in 350 ml of tetrahydrofuran (THF) in a 500 ml round bottom flask equipped with a side arm and dropping funnel with pressure equalizer.

0.25 mol of methyllithium (CH$_3$Li) were added dropwise as a 1.6 M solution in ether. Stirring of the solution was continued for three hours.

After gas evolution had ceased, 100 ml of THF containing 0.25 mol of 6-(4-methoxy-phenyl) 6-methyl-fulvene were added dropwise to the solution. Stirring of the solution was continued overnight.

The resulting solution was then washed with 200 ml of a saturated ammonium chloride aqueous solution, then with water.

After evaporation of the solvents, a powder was recovered on the surface of the water. Recrystallization by dissolving the powder in 500 ml chloroform and addition of excess ethanol at 2° C. yielded a powder.

Yield: 60%. M.P.: 189–190° C.

c. Preparation of the bridled metallocene

Reaction of the ligand with alkyllithium 10 g (0.0368 mol) of the ligand were dissolved in 200 ml THF in a 500 ml round bottom flask equipped with a side dropping funnel.

0.0736 mol of methyllithium were added dropwise as a 1.6 M solution in ether. Stirring of the solution was continued for three hours.

After gas evolution had ceased, the solvents were evaporated at 40° C. leaving a finely powdered product after about 2 hours.

Reaction of the metal salt with the lithiated ligand 0.0368 mol of the ligand dilithium derivative was dissolved in 175 ml of cold methylene chloride at −78° C.

A slurry of 0.0368 mol of ZrCl$_4$ in 175 ml of cold methylene chloride was poured in the flask containing the lithiated ligand solution. The mixture was stirred during two hours at −78° C., allowed to warm slowly to room temperature (23° C.) and stirred for an additional 12 hours.

Insoluble white LiCl was filtered off before crystallizing a powder by cooling the red solution to −20° C. for 12 hours.

After decantation, the crystalline powder was washed several times methylene chloride at −20° C. and isolated by removing the solvent under vacuum.

Yield: 76%.

Figure 2:
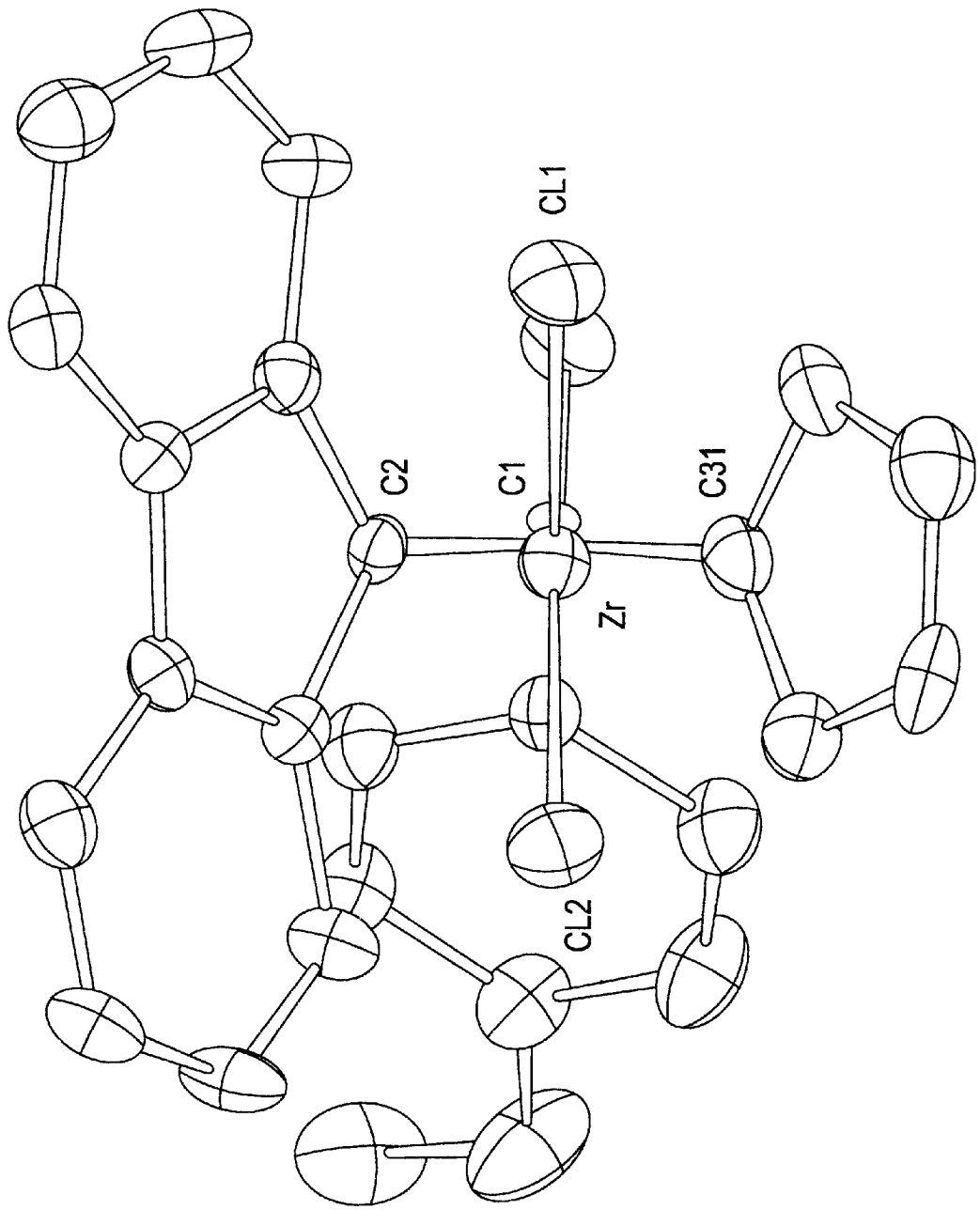

The structure of this metallocene compound is shown in FIGS. 1 and 2, which are two different perspectives of the molecular structure (excluding H atoms). Some important distances (expressed in $10^{-10}$ m) between atoms (named as in FIGS. 1 and 2, except for Z2 and Z31 which are the centroids of the C5 rings containing respectively C2 and C31) and angles (expressed in degrees) are given hereafter:

| Zr-C11 | 2.413 | Zr-Z2 | 2.26 |
|---|---|---|---|
| Zr-C12 | 2.425 | Zr-Z31 | 2.17 |
| Zr-C2 | 2.404 | Zr-C31 | 2.447 |
| Zr-C3 | 2.508 | Zr-C32 | 2.448 |
| Zr-C8 | 2.681 | Zr-C33 | 2.532 |
| Zr-C9 | 2.700 | Zr-C34 | 2.527 |
| Zr-C14 | 2.537 | Zr-C35 | 2.438 |
| C11-Zr-C12 | 99.9 | | |
| Z31-Zr-Z2 | 118.3 | | |
| C31-C1-C2 | 99.1 | | |
| C21-C1-C41 | 106.4 | | | d. Polymerization of propylene

Four polymerizations were carried out in a two-liter Buchi-type autoclave purged with nitrogen gas then kept at a temperature of 60° C. The catalyst and the co-catalyst (MAO, 10 ml of a 11 wt % solution in toluene) were precontacted during 3 minutes before being introduced in the reactor with 1 l of propylene; the pressure in the reactor was of 2.8 MPa. After 1 hour polymerization, the polymerization activity, the polymer bulk density, the polymer melting point, the polymer molecular weight (weight-average) and the stereoregularity (as shown by the rrrr value) were determined; the values are shown in Table 1.

TABLE 1

| Example | Cat (mg) | Activity (kg/g.h) | B.D. (g/ml) | M.P. (° C.) | $M_w$ kDa | rrrr (%) |
|---|---|---|---|---|---|---|
| 1.1 | 2.3 | 4.5 | 0.40 | 122.4 | 76 | 8.4 |
| 1.2 | 2.5 | 4.7 | 0.40 | 117.9 | 69 | 72.1 |
| 1.3 | 8.0 | 10 | 0.39 | 123.6 | 75 | 75.8 |
| 1.4 | 8.0 | 18 | 0.31 | 124.5 | 77 | 74.3 |
| 2 | 2.5 | 28 | 0.4 | 128.7 | 69 | 76.5 |
| 3 | 2.5 | 47 | 0.36 | n.d. | 73 | 77.8 |
| C1 | 2.0 | 190 | 0.06 | 137.1 | 93 | 84.2 |
| C2 | 2.0 | 127 | 0.07 | 134.8 | 109 | 82.9 |

EXAMPLE 2

Catalyst Based on $(Cp)(Flu)C(H)(p\text{-}Ph\text{-}SCH_3)ZrCl_2$ a. Preparation of the fulvene.

6-(4-methylthio-phenyl)-fulvene was prepared following the procedure described in example 1a, except that the reaction time was 15'.

Yield: 96% ; M.P.: 105–6° C.

b. Preparation of the ligand.

The ligand was prepared according to the procedure described in example 1b.

Yield: 53% ; M.P.: 186° C. (decomposition)

c. Preparation of the catalyst.

The catalyst was prepared according to the procedure described in example 1c.

Yield: 18% d. Polymerization of propylene

The procedure of example 1d was repeated, except as indicated in the Table; the pressure was of 2.6 MPa.

EXAMPLE 3

Catalyst Based on $(Cp)(Flu)C(H)(p\text{-}Ph\text{-}N(CH_3)_2)ZrCl_2$ a. Preparation of the fulvene.

6-(4-methylthio-phenyl)-fulvene was prepared following the procedure described in example 1a, except that the reaction time was 1 hour.

Yield: 89% ; M.P.: 106–7° C.

b. Preparation of the ligand.

The corresponding ligand was obtained according to the procedure described in example 1b.

Yield: 77% ; M.P.: 218–9° C.

c. Preparation of the catalyst.

The catalyst was prepared according to the procedure described in example 1c.

Yield: 22%.

d. Polymerization of propylene

In example 3, the procedure of example 1d was repeated, except as indicated in Table 1.

COMPARATIVE EXAMPLES

Catalysts Based on (Cp)(Flu)Rc

The catalyst systems were prepared and used as described in example 1a/1c/1d. In Comparative Example C1, the Rc bridge was methyl isopropyl methylidene, in C2 methyl isobutyl methylidene.

In addition to the bulk density of the polymer being lower than when using the catalysts according to the invention, the particle size was smaller, and the polymer contained a large amount of fines.

EXAMPLES 4 TO 6

Supported Catalyst

Pretreatment of the support gamma-$Al_2O_3$ (10 g) was heat treated for 4 hours. It was then suspended in toluene (Na-dried, 50 ml) and MAO (methylalumoxane, as 11 wt % solution in toluene) was added dropwise. The slurry was stirred for 30 min. at room temperature.

At the end of this period it was filtered and the solid so obtained was washed 2 times each with Na-dried toluene then with $CaH_2$-dried pentane and dried under vacuum.

Preparation of the supported catalyst.

Catalyst as described in example 3 was dissolved in toluene (Na-dried 20–30 ml). Pretreated gamma-$Al_2O_3$ was added and a slurry was obtained. It was stirred at room temperature for 30 minutes.

After decantation of the supernatant liquid, the solid was washed 3 times each with toluene, then with pentane ($CaH_2$-dried) and dried under vacuum.

The experimental conditions were as follows:

example 4:—heat treatment at 900° C.

0.5 g MAO/10 g alumina example 5:—heat treatment at 300° C.

1.4 g MAO/10 g alumina example 6:—heat treatment at 300° C.

2.5 g MAO/10 g alumina

Polymerization of propylene was carried out as described in example 1d, except as indicated in Table 2.

The results are indicated in Table 2. They demonstrate that the process of the invention is more efficient to improve morphology than deposition on a support.

TABLE 2

| Example | Catalyst/support (g/g) | Supported catalyst (g) | MAO (11 wt %) (ml) | Activity* (kg/g.h) | Bulk density (g/ml) |
|---|---|---|---|---|---|
| 4.1 | 0.02 | 1 | 3 | 1.8 | 0.30 |
| 4.2 | 0.01 | 1 | 3 | 4.0 | 0.30 |
| 5.1 | 0.02 | 1 | 3 | 1.4 | 0.35 |
| 5.2 | 0.01 | 1 | 3 | 1.2 | 0.35 |
| 5.3 | 0.01 | 1 | 10 | 1.1 | 0.35 |

TABLE 2-continued

| Example | Catalyst/support (g/g) | Supported catalyst (g) | MAO (11 wt %) (ml) | Activity* (kg/g.h) | Bulk density (g/ml) |
|---|---|---|---|---|---|
| 6.1 | 0.02 | 1 | 3 | 1.3 | 0.30 |
| 6.2 | 0.02 | 1 | 10 | 3.3 | 0.30 |

*calculated on the weight of metallocene used.

Obviously, numerous modifications and variations of the present invention are possible in light of the above teachings. It is therefore to be understood that within the scope of the appended claims, the invention may be practiced otherwise than as specifically described herein.

What is claimed is:

1. A bridged metallocene wherein the bridge carries a neutral electron-donor substituent, said substituent having the formula

$$R''' \: Z \: R''''_j$$

wherein
   $R'''$ is a rigid unsaturated hydrocarbon radical between Z and the bridge, such that Z is separated from the bridge by 2 to 5 carbon atoms,
   Z is nitrogen, phosphorus, oxygen or sulphur,
   $R''''$ is H or an alkyl, cycloalkyl, aryl, alkylaryl or arylalkyl having a maximum of 15 carbon atoms, each $R''''$ being the same or different,
   j is 1 when Z=O or S and 2 when Z=N or P.

2. A bridged metallocene wherein the bridge carries a neutral electron-donor substituent, said substituent having the formula

$$R''' \: Z \: R''''_j$$

wherein
   $R'''$ is an aromatic ring,
   Z is nitrogen, phosphorus, oxygen or sulphur,
   $R''''$ is H or an alkyl. cycloalkyl, aryl, alkylaryl or arylalkyl having a maximum of 15 carbon atoms, each $R''''$ being the same or different,
   j is 1 when Z=O or S and 2 when Z=N or P.

3. A bridged metallocene according to claim 2, wherein $R'''$ is p-phenylidene.

4. A bridged metallocene according to claim 1, wherein $R''''$ is hydrogen, methyl or ethyl.

5. A bridged metallocene according to claim 1, wherein $R''''$ is methyl or ethyl.

6. A bridged metallocene according to claim 1, wherein Z is oxygen or nitrogen.

7. A bridged metallocene having the formula

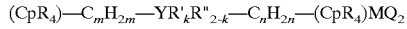
$$(CpR_4)-C_mH_{2m}-YR'_kR''_{2-k}-C_nH_{2n}-(CpR_4)MQ_2$$

wherein
   M is a Group IVb metal,
   Q is a hydrocarbyl radical having from 1 to 20 carbon atoms or a halogen, each Q being the same or different,
   Cp is a cyclopentadienyl ring,
   R is a substituent on a cyclopentadienyl ring and can be H or a hydrocarbon radical having 1 to 9 carbon atoms, each R being the same or different,
   each $(CpR_4)$ being the same or different,
   m is 0, 1, 2 or 3,
   n is 0, 1, 2, or 3,
   m+n is 0, 1, 2 or 3,
   k is 1 or 2
   Y is C or Si
   R' is a neutral electron-donor substituent of general formula

$$R''' \: Z \: R''''_j$$

wherein
   $R'''$ is a rigid unsaturated hydrocarbon radical between Z and the bridge such that Z is separated from the bridge by 2 to 5 carbon atoms
   Z is nitrogen, phosphorus, oxygen or sulphur,
   $R''''$ is H or an alkyl, cycloalkyl, aryl, alkylaryl or arylalkyl having a maximum of 15 carbon atoms, each $R''''$ being the same or different,
   j is 1 when Z=O or S and 2 when Z=N or P,
   $R''$ is as indicated for $R''''$.

8. A bridged metallocene according to claim 7, wherein M is titanium, hafnium or zirconium.

9. A bridged metallocene according to claim 8, wherein M is hafnium or zirconium.

10. A bridged metallocene according to claim 9, wherein M is zirconium.

11. A bridged metallocene according to claim 7, wherein Q is a hydrocarbyl radical having 1 to 3 carbon atoms or a halogen.

12. A bridged metallocene according to claim 11, wherein Q is chlorine or bromine.

13. A bridged metallocene according to claim 7, wherein m and n are 0.

14. A bridged metallocene having the formula

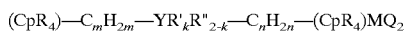
$$(CpR_4)-C_mH_{2m}-YR'_kR''_{2-k}-C_nH_{2n}-(CpR_4)MQ_2$$

wherein
   M is a Group IVb metal,
   Q is a hydrocarbyl radical having from 1 to 20 carbon atoms or a halogen, each Q being the same or different,
   Cp is a cyclopentadienyl ring,
   R is a substituent on a cyclopentadienyl ring and can be H or a hydrocarbon radical having 1 to 9 carbon atoms, each R being the same or different,
   each $(CpR_4)$ being the same or different,
   m is 0, 1, 2 or 3,
   n is 0, 1, 2, or 3,
   m+n is 0, 1, 2 or 3,
   k is 1 or 2
   Y is C R' is a neutral electron-donor substituent of general formula

wherein
- R''' is a rigid unsaturated hydrocarbon radical between Z and the bridge such that Z is separated from the bridge by 2 to 5 carbon atoms
- Z is nitrogen, phosphorus, oxygen or sulphur,
- R'''' is H or an alkyl, cycloalkyl, aryl, alkylaryl or arylalkyl having a maximum of 15 carbon atoms, each R'''' being the same or different,
- j is 1 when Z=O or S and 2 when Z=N or P,
- R'' is as indicated for R''''.

15. A bridged metallocene having the formula

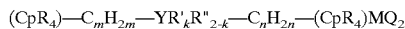

wherein
- M is a Group IVb metal,
- Q is a hydrocarbyl radical having from 1 to 20 carbon atoms or a halogen, each Q being the same or different,
- Cp is a cyclopentadienyl ring,
- R is a substituent on a cyclopentadienyl ring and can be H or a hydrocarbon radical having 1 to 9 carbon atoms, each R being the same or different,
- each ($CpR_4$) being the same or different,
- m is 0, 1, 2 or 3,
- n is 0, 1, 2, or 3,
- m+n is 0, 1, 2 or 3,
- k is 1 or 2
- Y is C or Si
- R' is a neutral electron-donor substituent of general formula

wherein
- R''' an aromatic ring
- Z is nitrogen. phosphorus, oxygen or sulphur,
- R'''' is H or an alkyl, cycloalkyl, aryl, alkylaryl or arylalkyl having a maximum of 15 carbon atoms, each R'''' being the same or different,
- j is 1 when Z=O or S and 2 when Z=N or P,
- R'' is as indicated for R''''.

16. A bridged metallocene according to claim 15, wherein R''' is p-benzylidene.

17. A bridged metallocene according to claim 7, wherein R'''' is hydrogen, methyl or ethyl.

18. A bridged metallocene according to claim 17, wherein R'''' is methyl or ethyl.

19. A bridged metallocene according to claim 7, wherein Z is oxygen or nitrogen.

20. A bridged metallocene according to claim 7, wherein R'' is hydrogen, an alkyl up to 4 carbon atoms or an aryl.

21. A bridged metallocene according to claim 20, wherein R'' is hydrogen or methyl.

* * * * *